United States Patent
Bono et al.

(10) Patent No.: US 12,096,946 B2
(45) Date of Patent: Sep. 24, 2024

(54) VERTEBRAL DISC CUTTER AND METHOD

(71) Applicant: GLOBUS MEDICAL, INC., Audubon, PA (US)

(72) Inventors: Peter L. Bono, Bingham Farms, MI (US); James D. Lark, West Bloomfield, MI (US); John S. Scales, Ann Arbor, MI (US)

(73) Assignee: Globus Medical, Inc., Audubon, PA (US)

(*) Notice: Subject to any disclaimer, the term of this patent is extended or adjusted under 35 U.S.C. 154(b) by 255 days.

(21) Appl. No.: 17/583,850

(22) Filed: Jan. 25, 2022

(65) Prior Publication Data

US 2022/0249103 A1 Aug. 11, 2022

Related U.S. Application Data

(60) Provisional application No. 63/142,719, filed on Jan. 28, 2021.

(51) Int. Cl.
*A61B 17/16* (2006.01)

(52) U.S. Cl.
CPC ...... *A61B 17/1617* (2013.01); *A61B 17/1624* (2013.01); *A61B 17/1631* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1659; A61B 17/1662; A61B 17/1671
See application file for complete search history.

(56) References Cited

U.S. PATENT DOCUMENTS

| | | | | |
|---|---|---|---|---|
| 5,626,444 | A * | 5/1997 | Campian | B23C 3/00 408/67 |
| 6,063,088 | A * | 5/2000 | Winslow | A61F 2/4611 606/279 |
| 6,234,725 | B1 * | 5/2001 | Campian | B23Q 11/0046 408/67 |
| 8,273,088 | B2 * | 9/2012 | Zalenski | A61B 17/1671 606/279 |
| 8,353,912 | B2 * | 1/2013 | Darian | A61B 17/320068 606/279 |
| 8,449,545 | B2 * | 5/2013 | Sidebotham | A61B 17/1637 606/80 |
| 8,460,298 | B2 * | 6/2013 | O'Donoghue | A61B 17/1615 606/80 |
| 8,845,638 | B2 * | 9/2014 | Siegal | A61B 17/1671 606/180 |
| 9,033,986 | B2 * | 5/2015 | Nelson | A61B 17/1624 606/171 |
| 9,232,953 | B2 * | 1/2016 | Bono | A61B 17/1615 |
| 11,006,967 | B2 * | 5/2021 | Woodard | A61B 17/1604 |

(Continued)

FOREIGN PATENT DOCUMENTS

| | | | | |
|---|---|---|---|---|
| EP | 1764046 | A2 * | 3/2007 | ......... A61B 17/1659 |
| EP | 2404689 | A1 * | 1/2012 | ......... A61B 17/1615 |

(Continued)

*Primary Examiner* — Eric S Gibson

(57) ABSTRACT

An improved surgical tool including a cutter that will accumulate cut disc material during operation. One form can form a bore while another form can be used as a side cutter. The tool can be used as a rotary and/or reciprocating cutter.

5 Claims, 2 Drawing Sheets

(56) References Cited

U.S. PATENT DOCUMENTS

| | | | |
|---|---|---|---|
| 11,766,266 B2* | 9/2023 | Bono | A61B 17/1659 |
| | | | 606/180 |
| 2007/0233127 A1* | 10/2007 | Tuke | A61B 17/1668 |
| | | | 606/79 |
| 2007/0233131 A1* | 10/2007 | Song | A61B 17/1671 |
| | | | 606/79 |
| 2008/0047143 A1* | 2/2008 | Quan | A61C 3/02 |
| | | | 29/896.1 |
| 2009/0048602 A1* | 2/2009 | O'Donoghue | A61B 17/1615 |
| | | | 606/80 |
| 2014/0100574 A1* | 4/2014 | Bono | A61B 17/1615 |
| | | | 606/80 |
| 2015/0093204 A1* | 4/2015 | Raynor | B23C 5/1081 |
| | | | 76/115 |
| 2019/0290290 A1* | 9/2019 | Bono | A61B 17/1659 |
| 2020/0046377 A1* | 2/2020 | Woodard | A61B 17/1604 |
| 2022/0249103 A1* | 8/2022 | Bono | A61B 17/1659 |

FOREIGN PATENT DOCUMENTS

| | | | | |
|---|---|---|---|---|
| FR | 2921819 A1 * | 4/2009 | | A61B 17/1615 |
| WO | WO-2022123548 A1 * | 6/2022 | | |

* cited by examiner

VERTEBRAL DISC CUTTER AND METHOD

CROSS-REFERENCE TO RELATED APPLICATION(S)

This application is a non-provisional application claiming priority to U.S. Provisional Patent Application No. 63/142,719 filed on Jan. 28, 2021 and titled "Vertebral Disc Cutter and Method," the contents of which is incorporated by reference herein in its entirety for all purposes.

FIELD

The present disclosure generally relates to cutting tools; and more particularly, to a cutting tool having cutting teeth projecting from a generally cylindrical support or removing disc material between adjacent vertebrae.

BACKGROUND

Disc surgery is a common procedure to alleviate pain caused by a herniated or degenerated disc. A surgeon will use a power operated cutting tool to cut out all or a portion of the problematic disc. In the disc removal, the cut out disc material needs to be removed, preferably continuously, to keep the surgical site clear. Such surgery can be done directly by a surgeon with a surgical robot assisting the surgeon, or by a computer operated surgical robot. The disc material removal can be done with a rotary cutter, an oscillating cutter, or a cutter that both oscillates and rotates.

Currently, existing systems provide cutting tools that remove material when rotated. These tools typically include one or more helixes cut into the tool; the helixes all arranged in the same direction and parallel if more than one helix is present. The helix may be formed for left hand rotation or for right hand rotation of the cutting tool. The leading edge of each helix is provided with a sharpened edge that cuts the material when rotated, while the helix moves the cut material away from the cutting action. The rear edge of the helix is provided with relief so as not to drag on the edge of a cut surface.

For example, U.S. Pat. No. 9,232,953 issued to Bono, provides a cutting tool for bone, cartilage and disc material that includes at least one helix arranged in a first direction and at least one helix arranged in a second direction so that the cutting tool can be oscillated back and forth to effect cutting. The tool is moved sideways to effect cutting, but is not very effective at forming a bore hole. Such a tool is more effective when the cut material is removed separately, as by suction.

Therefore, it would be desirable to provide a cutting tool that can cut disc material and simultaneously capture the cut material while cutting.

Thus, the present disclosure provides a surgical cutting tool which overcomes the disadvantages of prior art surgical cutting tools by providing simultaneous cutting and cut material capture.

SUMMARY

In accordance with the disclosure, a cutting tool for bone, cartilage, and disc removal including a body having distal end, a proximal end, an outer surface, and a hollow interior chamber, wherein the interior chamber is defined by an interior surface. The cutting tool further includes a plurality of cutting teeth extending inwardly from the interior surface and configured to engage and cut disc material during a surgical procedure, a bore, disposed at the proximal, configured to engage a power source; and a through opening positioned adjacent to the proximal end configured to provide access from an exterior of the body into the interior chamber.

In accordance with the disclosure, a cutting tool for bone, cartilage, and disc removal including a body configured to be mounted to a shaft of a power source and a plurality of cutting teeth extending outward from an exterior surface of the body, wherein each of the plurality of cutting teeth have a post connected to the exterior surface of the body and a cutter head disposed at a distal end of each post.

DETAILED DESCRIPTION OF THE DISCLOSURE

Figure 1:
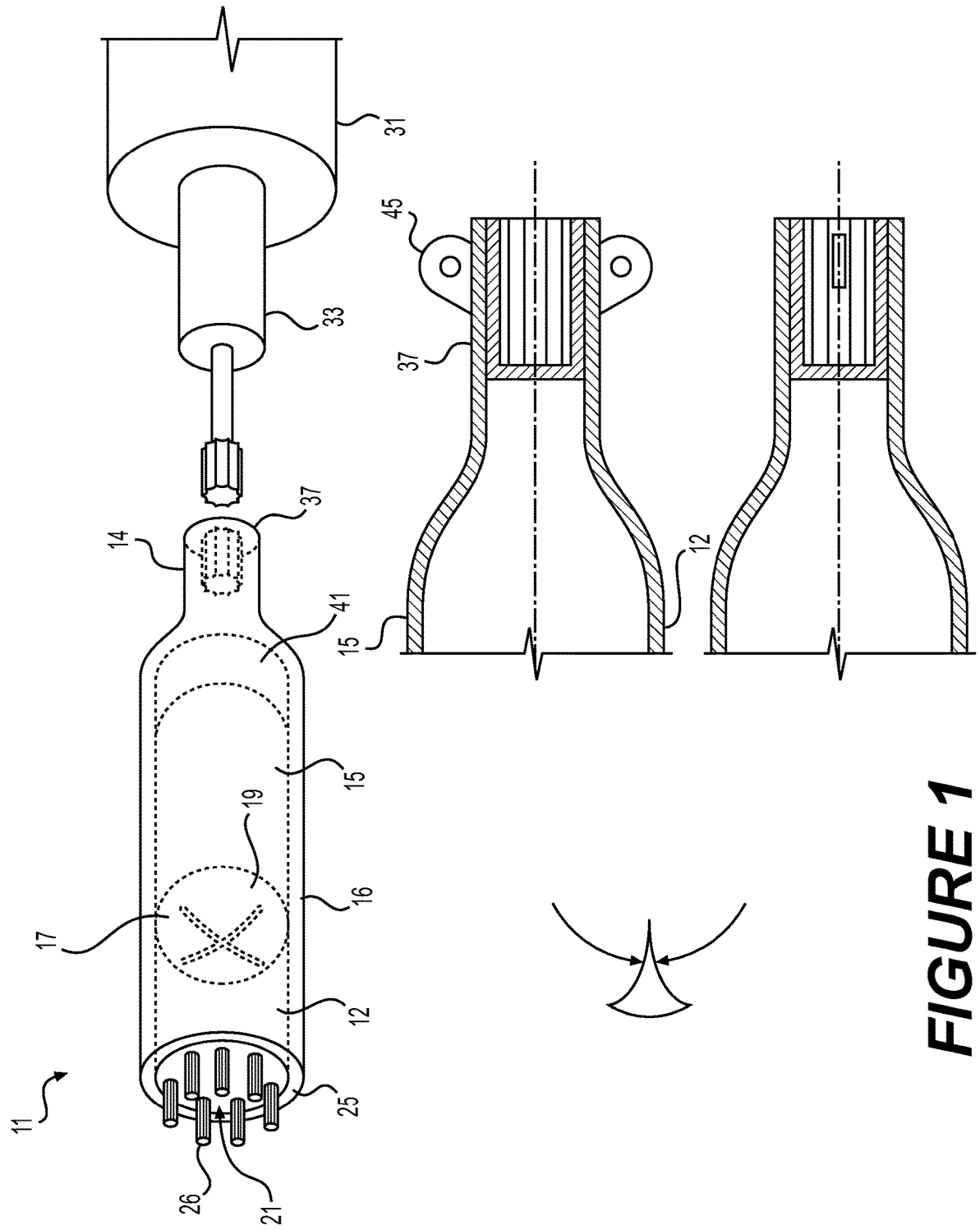
FIG. 1 is an isometric view of a rotary cutter operable for boring a hole using internal cutting teeth.

FIG. 1 illustrates an exemplary embodiment of a disc cutting tool 11 that, at least at the distal end portion 14, is tubular and preferably generally cylindrical on an outer surface 15. As shown, the tool 11 has a body 12 that is tubular, having a hollow interior chamber 17 defined by an interior surface 19 that, at the end portion 14, is also generally cylindrical. A plurality of cutting teeth 21 extend inwardly from the surface 19 and are operable to engage and cut disc material during a surgical procedure. The free end 25 of the tool 11 can be provided with cutters 26, such as formed teeth or abrasive grit, bonded to the tool 11. It has been found though that, for disc type material, cutting with the cutters 26 is not necessary. The tool 11 can be made of any suitable material, such as hardened steel, like stainless steel.

The tool 11 is provided with attachment means operable for attaching the tool 11 to a power source 31 with the drive mechanism that can effect either rotary motion of the tool 11 and/or reciprocating oscillation of the tool 11. Such power sources 31 are known in the art, as exemplified by that disclosed in U.S. Pat. Nos. 10,194,922 and 10,835,263; the disclosure of which are incorporated herein by reference. Such power sources typically include an electrically powered motor (not shown). An air-powered motor could also be used. The power source 31 is provided with an output shaft 33 that is suitably configured for attachment of the tool 11 thereto, preferably in the toolless manner. Preferably, the longitudinal axis of the body 12 is aligned with the longitudinal axis of the shaft 33. Such attachment can be by a splined shaft 33 fitting into a female splined bore at the proximal end 37 of the tool 11. A click lock connection could also be used, as well as a clamp type or ball and detent connection. The output shaft 33 can also be a surgical implement, such as a cutter.

A plurality of cutting teeth 21 project generally inwardly from the surface 19 and are configured to engage and cut disc material during operation of the tool 11. The teeth 21 can be of any suitable shape, such as triangular like teeth found on a rasp. They could also be rounded, rectangular or the like, with the leading edge or edges being sharp. As shown, there are a plurality of teeth 21 positioned in spaced apart relationship radially about the surface 19, and also positioned in spaced apart relationship longitudinally along the surface 19.

As shown, the tool 11 can be provided with means to help evacuate the interior chamber 17 of collected cut disc material. As shown, a through opening 41 is positioned adjacent the proximal end 37 that provides access from the exterior 16 of the tool 11 into the interior chamber 17. A suitable implement can be provided, such as a brush or rod, which can be inserted into the opening 41 to push the collected disc material out of the open free end 25. The proximal end 37 can be provided with outwardly extending deflection tabs 45 to assist in material removal.

Figure 2:
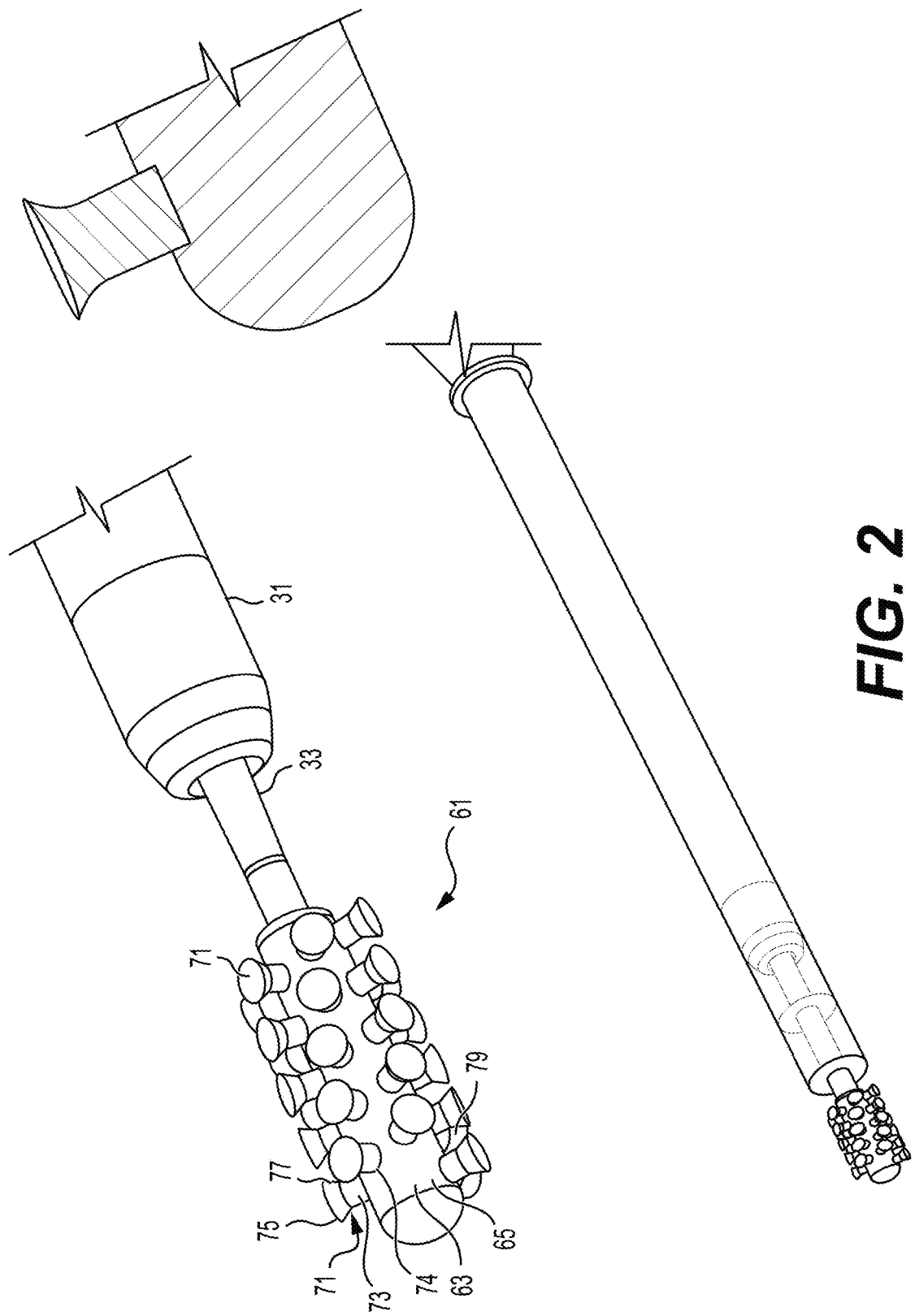
FIG. 2 is an isometric view of a cutter that is operable for cutting disc material in rotary and/or reciprocating motion.

FIG. 2 illustrates an exemplary embodiment of a cutter, and is designated generally 61. As described above, the power source 31 can have a drive mechanism (not shown) that effects either or both rotary motion of its output shaft 33 and reciprocal oscillating motion of the tool 61. As shown, the tool 61 has a body 63 that is suitably mounted to the shaft 33, either in a removable manner or a permanent manner as desired. Such mounting is described above. For convenience of manufacture, the exterior surface 65 of the body 63 is generally cylindrical, having its longitudinal axis aligned with the longitudinal axis of the shaft 33.

A plurality of cutting teeth 71 are secured to the body 63 and project generally radially outwardly from the exterior surface 65 of the body 63. As shown, the teeth 71 each have a post 73 that projects generally radially outwardly from the surface 65. The posts 73 have a proximal end 74 secured to the body 63. The posts 73 have a distal free end portion forming a cutter head 75, with the cutting edge 77 shaped to effect cutting during both rotary motion and/or oscillating motion of the cutter 61. The cutter heads 75 are larger than their respective posts 73, forming disc material collection spaces 79 between the heads 75 and body 63. As shown, the cutter heads are shaped frustoconically. In a preferred embodiment, the cutting edges 77 are generally circular, presenting a sharp edge to disc material whether the tool 61 is rotating and/or oscillating. Other shapes will work, such as triangular, hexagonal and the like.

As shown, the teeth 71 are positionally arranged on the body 63 to substantially always, during operation, present a cutting edge to the engaged disk material, providing substantially complete cutting coverage without gaps in disc material removal regardless of cutting mode. As shown, the teeth are in longitudinal columns and in circumferential rows. As shown, the rows and columns are both helical arrayed. Other positioning formats can be used to achieve the same functional cutting paths.

The tools 11 and 61 are used in disc surgery. During operation, cut disc material can be accumulated by the tool for later removal from the tool. The tools can be operated rotationally and/or reciprocally to effect disc cutting.

All patents and publications mentioned in this specification are indicative of the levels of those skilled in the art to which the disclosure pertains. All patents and publications are herein incorporated by reference to the same extent as if each individual publication was specifically and individually indicated to be incorporated by reference.

It is to be understood that while a certain form of the disclosure is illustrated, it is not to be limited to the specific form or arrangement herein described and shown. It will be apparent to those skilled in the art that various changes may be made without departing from the scope of the disclosure and the disclosure is not to be considered limited to what is shown and described in the specification and any drawings/figures included herein.

One skilled in the art will readily appreciate that the present disclosure is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the disclosure and are defined by the scope of the appended claims. Although the disclosure has been described in connection with specific preferred embodiments, it should be understood that the disclosure as claimed should not be unduly limited to such specific embodiments. Indeed, various modifications of the described modes for carrying out the disclosure which are obvious to those skilled in the art are intended to be within the scope of the following claims.

What is claimed is:

1. A cutting tool for bone, cartilage, and disc removal comprising:
   a body configured to be mounted to a shaft of a power source; and
   a plurality of cutting teeth extending outward from an exterior surface of the body, wherein each of the plurality of cutting teeth have a post connected to the exterior surface of the body and a cutter head disposed at a distal end of each post, wherein each cutter head is circular with a 360 degree sharp cutting edge configured to remove tissue, and wherein each cutter head is shaped frustoconically such that each cutter head is wider than each post.

2. The cutting tool of claim 1, wherein the plurality of teeth are arranged in longitudinal columns and circumferential rows.

3. The cutting tool of claim 2, wherein the longitudinal columns and the circumferential rows are helically arrayed.

4. The cutting tool of claim 1, wherein the body is configured to be removably mounted to the shaft.

5. The cutting tool of claim 1, wherein the cutter heads are wider than the respective posts forming disc material collection spaces between the cutter heads and the body.

* * * * *